Dec. 6, 1949. T. B. STRIBLING, JR Plant Pat. 904

PEACH TREE

Filed April 14, 1947

INVENTOR
Thos. B. Stribling Jr.

Webster Turnbull
ATTY.

Patented Dec. 6, 1949

Plant Pat. 904

UNITED STATES PATENT OFFICE

904

PEACH TREE

Thomas Burton Stribling, Jr., Merced, Calif.

Application April 14, 1947, Serial No. 741,387

1 Claim. (Cl. 47—62)

The present discovery relates to a new and distinct variety of peach tree; the variety being characterized by seeds which produce seedlings having high resistance to nematode infestation and crown gall, and therefore especially useful as a root stock for drupe fruits budded or grafted thereon.

The present discovery resulted from experimentation with approximately three thousand seedlings of ten or twelve mixed varieties of ornamental flowering *Prunus persica*. The experiments were primarily conducted in an effort to discover a means to control crown gall. One of these flowering peach seedlings was a seed sport which proved to be very highly resistant to nematode, as well as crown gall.

Budded seedlings of this nematode and crown gall resistant variety were tested in experimental plots in the following manner.

Such budded seedlings were planted in rows alongside other budded seedlings of these supposedly resistant varieties in general horticultural use, i. e. Shalil, Yunnan, and Bokhara. The rows of such seedlings, including the seedlings of the present variety, were all budded with the same top varieties of drupe fruits and were planted in soil known to be badly infested throughout the nematode. All of these rows of seedlings received identical care, the same irrigation; the same fertilization; the same spraying; and the same pruning. The seedlings of the herein claimed variety produced a tree which effectively resisted the Nematoda and crown gall; being much more uniform and vigorous in growth than the other above mentioned root stock varieties. The other varieties of root stock seedlings in the test all showed nematode infestation and greater susceptibility to crown gall.

The present variety of peach tree has been asexually reproduced and it has been ascertained that the reproductions maintain in full the unique characteristic of the original tree; to-wit, its ability to yield seeds which produce seedlings having high resistance to nematode infestation and crown gall, which makes them desirable as a root stock for drupe fruits.

Figure 1:
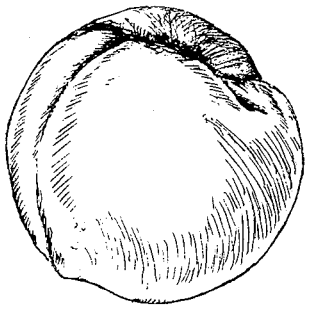
Fig. 1 is a view, taken from the suture side, showing generally the configuration of the fruit borne by the present variety.
Figure 2:
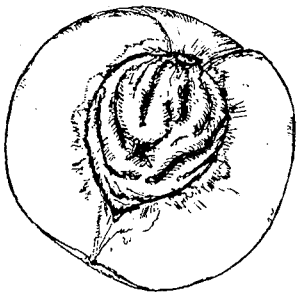
Fig. 2 is a sectional view of the fruit with the stone exposed.
Figure 3:
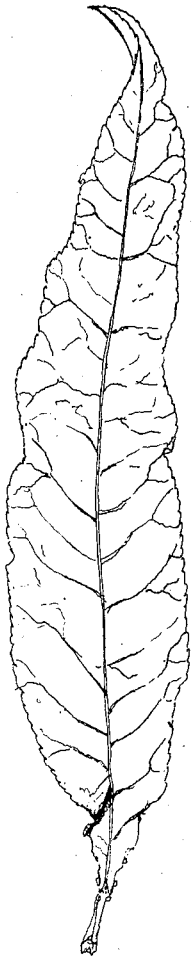
Fig. 3 is an elevation of one of the leaves.

While the novel feature of the present variety resides not in visual characteristics of its fruit or leaves, drawings of the same are presented herein for the purpose of accurate pomological identification.

Referring now in detail to the new and distinct variety of peach tree, the following is a detailed description thereof:

*Tree.*—The tree is large, vigorous, spreading, dense, and round topped; being hardy and a productive and regular bearer. However, the fruit is of no appreciable value as a commercial fruit for eating, canning, or drying. The value of the tree resides primarily in its use as a nematode resistant root stock for drupe fruits. The trunk of the tree is of medium size and medium bark texture; the branches being of medium size and texture, and relatively dull dark brown.

The lenticels are medium in number and size.

*Leaves.*—The leaves of the variety average 6½″ in length and 1½″ in width, being of medium size, ovate, acuminate, and acutely pointed. Also, the leaves are of medium thickness and in color are medium green, being smooth and having a crenate, finely serrate margin.

The petiole is of medium length and thickness. The glands average four to six in number, are alternate, or regular size, globose, green in color, and appear mostly on the petiole, although occasionally on the blade.

*Flowers.*—The flower buds are half hardy, of medium small size and medium short length, being pointed, free, and slightly pubescent. The flowers bloom in mid season at approximately the same time as the Elberta peach, which normally is in full bloom in the Merced, California, area about March 10th. The flowers are large, and vary in color from pink to red.

*Fruit.*—The fruit ripens in the latter part of August, and is described as follows:

The fruit is of medium size, having an average diameter axially of 2⅜″ and 2¼″ transversely in the suture plane. The fruit is uniform in shape, symmetrical and globose; the suture being an inconspicuous line, which is relatively shallow.

The ventral surface is rounded slightly with equal lips.

The cavity is flaring and is elongated in the suture plane, and shows mostly on the suture side of the fruit; such cavity averaging ¼″ in depth and ½″ in breadth.

The base is rounded, the apex is short, and the stem averages ¼″ in length and is of medium size, with weak adherence to the stone.

The skin of the fruit is thin, of medium thickness, and bitter, with slight tendency to crack. In color the skin has considerable red blush.

Down is moderate to scant, short, and does not roll up when rubbed.

The flesh of the fruit is of white color, reddish next to the stone. The surface of the pit cavity is red with pink fibers. The texture is soft and melting, the fibers few, and the flesh ripens evenly. The flavor of the flesh is mild with distinct aroma, and the eating quality is fair, even though the fruit is not intended for commercial use.

*Stone.*—The stone is free and when parted from the flesh retains short fiber-like threads along the ridges. The stone is of medium size, averaging 1¼″ in length, 1″ in breadth, and ⅝″ in thickness, such stone being ovoid in form. The base is oblique, the hilum narrow, and the apex rounded. The sides are equal, but curved on the right side. The surface is regularly furrowed, ridged, and pitted throughout; the pits are angular; and the ventral edge is without wing throughout. The dorsal edge is full, with shallow groove throughout, and the ridges are continuous. The color of the stone is brown and it has a slight tendency to split.

The herein described peach tree may vary in slight details due to climatic and soil conditions under which the variety may be grown.

As hereinbefore indicated, the fruit is not adapted, nor has it any appreciable value, for eating, canning, or drying. However, the fruit is harvested when ripe to the end that the seeds may be recovered and used to produce root stock seedlings for drupe fruit; the nematode and crown gall resistant characteristics of these direct seedlings of the variety, when used as root stock, having heretofore been described.

Having thus described my discovery, I claim:

A new and distinct variety of peach tree, which is a sport of *Prunus persica*, characterized by the seeds which produce seedlings having greater resistance to nematodes and crown gall as compared to other known peach root stocks including Yunnan, Shalil, and Bokhara.

THOMAS BURTON STRIBLING, Jr.

No references cited.